United States Patent [19]
Cox et al.

[11] Patent Number: 5,807,587
[45] Date of Patent: Sep. 15, 1998

[54] ALDEHYDE AND/OR ANTIMICROBIAL COMPOSITION FOR REDUCTION OF ANIMAL WASTE ODORS

[76] Inventors: James P. Cox; Robert W. Duffy Cox, both of 246 E. Bartlett Rd., Lynden, Wash. 98264

[21] Appl. No.: 799,104

[22] Filed: Feb. 11, 1997

Related U.S. Application Data

[63] Continuation of Ser. No. 586,603, Jan. 16, 1996, abandoned.

[51] Int. Cl.[6] ........................................................ A61L 9/01
[52] U.S. Cl. ..................... 424/76.6; 424/767; 514/494; 514/499; 514/694; 514/699
[58] Field of Search .................. 424/76.6, 76.7; 514/494, 499, 694, 899

[56] References Cited

U.S. PATENT DOCUMENTS

| | | | |
|---|---|---|---|
| 1,408,535 | 3/1922 | Ressler | 210/59 |
| 3,446,733 | 5/1969 | Shell | 210/59 |
| 3,505,217 | 4/1970 | Morico | 210/59 |
| 3,843,545 | 10/1974 | Heuston | 252/181 |
| 4,254,008 | 3/1981 | Krsek | 260/33.4 |
| 4,364,835 | 12/1982 | Cheh | 210/759 |
| 4,385,996 | 5/1983 | McCarthy | 210/759 |
| 4,517,369 | 5/1985 | Marinak et al. | 546/345 |
| 4,666,610 | 5/1987 | Kuhns | 210/749 |
| 4,847,143 | 7/1989 | Watanabe et al. | 424/288 |
| 4,894,452 | 1/1990 | Stephan | 544/194 |
| 4,909,986 | 3/1990 | Kobayashi et al. | 422/4 |
| 4,931,360 | 6/1990 | Hoshino et al. | 428/328 |

FOREIGN PATENT DOCUMENTS

| | | |
|---|---|---|
| 212837 | 3/1987 | European Pat. Off. . |
| 2 623 717 | 6/1989 | France . |
| 57-166166 | 10/1982 | Japan . |
| 57-49220 | 10/1982 | Japan . |
| 58-10051 | 1/1983 | Japan . |
| 60-40057 | 3/1985 | Japan . |
| 62-207463 | 9/1987 | Japan . |
| 63-249565 | 10/1988 | Japan . |
| 64-70062 | 3/1989 | Japan . |
| 2-74259 | 3/1990 | Japan . |
| 823311 | 4/1979 | U.S.S.R. . |
| 1152388 | 5/1969 | United Kingdom . |

OTHER PUBLICATIONS

Nelson Herwig, *Toxic Chloramine Induced Intravascular Hemolytic Anemia In Fish*, published prior to 1985.
George C. Blaslola, "Chloramines", *Pet Age*, Jul. 1984.
George R. Helz and Lynn Kosak–Channing, "Dechlorination of Wastewater and Cooling Water", *Environ. Sci. Technol.*, vol. 18, No. 2, 1984.
*Dechlorination* (brochure), Allied Chemical; Corporation, New Jersey, copyright 1977.
Fredrick Warner Wheaton, *Aquacultural Engineering*, pp. 608–612, 1977.
Morrison & Boyd, *Organic Chemistry*, pp. 639–641, 1966.
J. Frederic Walker, *Formaldehyde*, Reinhold Publishing Corporation, New York, 1944.
Non–Formaldehyde Products brochure, *Conquer*, J&J, publication date unknown.

*Primary Examiner*—James H. Reamer
*Attorney, Agent, or Firm*—Lyon & Lyon LLP

[57] ABSTRACT

A composition and method for preventing and/or reducing stench and septicity from animal waste comprising a sulfur and oxygen-bearing component and one or more aldehydes and/or one or more ketones. The sulfur and oxygen-bearing component is selected from the group consisting of sodium bisulfite, potassium bisulfite, lithium bisulfite, sodium metabisulfite, potassium metabisulfite, lithium metabisulfite, sodium hydrosulfite, potassium hydrosulfite, lithium hydrosulfite and hydrogen sulfite. The aldehyde is selected from the group consisting of formaldehyde, glyoxal, glutaraldehyde, benzaldehyde, acetaldehyde, butyraldehyde, cinnamaldehyde, anisaldehyde, salicylaldehyde, citral, glycolic aldehyde, paraldehyde, metaldehyde, heptylaldehyde, octylaldehyde and decylaldehyde. The ketone is selected from the group consisting of diacetyl, ionone, pseudo-ionone, acetylacetone, 3-buten-2-one, mesityl oxide, acetone, methyl ethyl ketone, diethyl ketone and dipropyl ketone. The composition and method also include the addition of a surfactant and/or metal thereto.

4 Claims, No Drawings

ALDEHYDE AND/OR ANTIMICROBIAL COMPOSITION FOR REDUCTION OF ANIMAL WASTE ODORS

This application is a continuation application of copending application Ser. No. 08/586,603, filed on Jan. 16, 1996, now abandoned.

BACKGROUND OF THE INVENTION

The present invention pertains to treating animal, including human, waste to reduce stench and septicity. More specifically, the present invention is for highly effective, safety improved chemical compositions and methods for treating body wastes to reduce stench and septicity which can replace certain aldehydes.

Aldehydes are known to be effective primary treating aids, but exhibit significant degrees of toxicity in the free state, rendering them unsafe for handling and use. Formaldehyde and glutaraldehyde have long been known to be effective body waste treating aldehydes for reducing stench and septicity. Both are toxic aldehydes existing under all ambient conditions in both liquid and volatile form. The vapors from both of these aldehydes are toxic to life upon ingestion, contact, and when breathed. Depending upon concentrations and means of contact, injuries can range from dermatitis to death.

Formaldehyde has long been used as a direct additive to body wastes. Formaldehyde is a very good sterilant and bactericide used within its limitations. Formaldehyde is known to be a very poor penetrant of biological matter and is consequently of somewhat questionable value as a microbicide under many conditions.

Formaldehyde (HCHO) is commercially offered as a 37% to 50% aqueous solution. Its properties: Strong pungent stench, vap d 1.067 (ait=1.000), at −20/4C vap d 0.815, bp −19C. It is a lachrymator, carcinogen, toxic by inhalation, and strong irritant. Threshold limit value (TLV): 1 ppm in air. $LD_{50}$ orally in rats: 0.80 g/kg. Vapors are intensely irritating to mucous membranes. Skin contact may produce irritant dermatitis.

Formaldehyde also exhibits significant activity with respect to reduction of stench from body wastes. Despite formaldehyde's poor penetrating qualities, it is effective against stench by both physical and volatile-to-volatile contact. Body waste stench treated with formaldehyde is dramatically, but not entirely, reduced. There are always characteristic, residual qualities of stench which seem unamenable to reduction by formaldehyde. This may not, but in many instances probably does, relate to the same functional characteristics which make formaldehyde a poor penetrant of body waste matter; i.e., it lacks adequate solventizing qualities to provide for adequate contact with microbes and stenchophoric elements inherent in the wastes. Formaldehyde reacts poorly, if at all, against lipidaceous moieties of any type. This includes many of those portions of protein breakdown products which contain lipids or carboxylic groups, as well as lipids per se, associated with body wastes. Upon the oxidative and enzymatic breakdown of lipids, fatty acids, which represent a very strong class of stench molecules, will be released. Also, many amines contain carboxylic groups which become freed with ammonia, or in association with amino nitrogen and sometimes sulfur volatiles, as nitrogen/fatty acid and nitrogen/sulfur/fatty acid complexes. These classes of stench molecules represent the majority of those associated with the decomposition of most protein/lipid containing biowastes, such as body wastes. Formaldehyde is not, as a rule, very effective against lipids or fatty acids or fatty acid complexes. In liquid, solid or volatile form it is not lipid soluble and is not effective against these stench volatiles. Used alone, formaldehyde cannot fully meet the objects of the present invention, stench prevention or reliable reduction of septicity.

Despite the above limitations, for a great many years formaldehyde has been used with moderate effect in one form or another for purposes of reducing stench and septicity of body wastes. Chemical product reviews driven by environmental and health safety concerns over the past several decades have, however, made it clear that formaldehyde is a carcinogen. Its vapors are irritating and while long known to be toxic to human life, it is now also known to be a carcinogen. This, of course, does not mean that formaldehyde cannot, or should not, be used under any circumstances, but that uses should be altered to conform with that awareness of its toxic and carcinogenic nature, or alternatives should be sought. Any treatment for body wastes that would be likely to result in persons being exposed to fugitive formaldehyde volatiles should not be used. This is most particularly true where the fugitive formaldehyde could be trapped in an enclosed environment, such as a portable toilet module, recreational vehicle and the like, where human beings will be certain to visit. Moreover, it should not be used even when the fugitive formaldehyde is not likely to be concentrated, such as where a user, worker or other person may be chronically exposed (for example, when septic tanks are pumped, portable toilets are emptied, or marine or recreational vehicles are used or when formaldehyde liquids are openly poured into body waste receptacles).

In recent years many manufacturers of products for use with body wastes, being aware of the problems with formaldehyde, have gone to glutaraldehyde as an alternative. While glutaraldehyde does have the advantage of a lower vapor pressure, and is considered somewhat less toxic than formaldehyde, it still suffers from all of the same disadvantages of formaldehyde.

Glutaraldehyde ($C_5H_8O_2$) has a vapor pressure of 17 mm (20C) and liq. density of d 0.72. It is an irritant and carcinogen. TLV ceiling is 0.2 ppm in air. $LD_{50}$ of 25% solution orally in rats: 2.38 ml/kg; by skin penetration in rabbits: 2.56 ml/kg.

Addition of formaldehyde and glutaraldehyde to body wastes can result in some reduction of stench. The mixture can react volatile to volatile with amino nitrogens and freed ammonia. Employed under conditions of high moisture and mechanical agitation, the mixture can influence substantially the reduction of ongoing stench from microbial and indigenous digestive activities upon body wastes. If agitated adequately with body wastes, formaldehyde is not only a powerful microbicide but also can arrest the decomposition of proteins and all species of protein breakdown products, including amino acids. The form of reaction involves strong cross bonding as well as other reactions with proteins and derivative products including peptides, amino acids, urea nitrogen and ammonia. The bonds are strong and resistant to decomposition, so stability can be quite good. Despite its deficiencies, used singularly formaldehyde has been, and would remain, a powerful basic control agent for combined stench and septicity control of body and other bioorganic wastes where proteins and protein products are prominent. Unfortunately, the on-going use of either formaldehyde of glutaraldehyde cannot be justified and should not be continued in view of its significant and clear threat to human health.

Quats can be useful for cleaning septic body wastes from surfaces and consequently may be employed advantageously, as may other surfactants and microbicides, in an accessory capacity to methods and products of the present invention. Quaternary ammonium products (quats) have long been used as surfactants of choice for cleaning biological wastes of all sorts and varieties, including body wastes. For controlling stench and septicity, they are inadequate and impractical under the necessary use conditions discussed herein. Quats and other cationics are insufficiently concentrated for the uses discussed herein. The stench-controlling factor associated with quats is not related to direct action with stench volatiles or even non-volatile stench precursor molecules. Quats act only on contact and not volatile-to-volatile, so they cannot react at all with stench molecules already present.

In relatively high concentrations, and when intermixed with body wastes and adequate water as occurs during washing, quats can indirectly reduce stench by killing many of the microbes, and thereby reduce stench volatiles associated with that pathway of stench formation. Reduction of the microbes is equivalent to reduction in septicity.

Quats do not react directly with stench volatiles and do not prevent enzymatic or digestive acid decomposition. They cannot effectively or economically reduce microbial populations (stench or septicity) under conditions of use within the field of the present invention. For example, the addition of an equivalent measure of quats to formaldehyde in a portable toilet would reduce none of the volatiles associated with incoming body wastes, they would not react with stench molecules diffusing over time from the body wastes, they would not prevent the ongoing decompositionally generated stench molecules derived from ongoing artifactual digests, they would not prevent the continued diffusion through the body wastes of those stench molecules, and they would not achieve adequate contact without mechanical agitation with microbes underneath superficial body waste layers to prevent increased septicity and stench generated therefrom.

In short, the addition of quats under these circumstances would do little to reduce or prevent the formation of stench or septicity of body wastes. Under the given circumstances, quats are less able to penetrate than formaldehyde since they exhibit no significant vapor gradient effectiveness against stench molecules, microbes, fermentation metabolites, artifactual digests or by-products from their ongoing activities. Provided adequate quantities are used to clean body wastes with other conditions being present such as copious water and mechanical agitation to provide contact and emulsification with body wastes, quats can achieve a small degree of effectiveness to control stench by indirectly preventing its formation from microbial fermentation. In conjunction with application under appropriate conditions, the concentration of quats to body waste determines effectiveness; and to the degree that microbes are killed, septicity and (up to a point) stench are reduced accordingly. Quats can be useful for cleaning septic body wastes from surfaces and consequently may be employed advantageously, as may other surfactants and microbicides, in an accessory capacity to methods and products of the present invention.

Even less toxic aldehydes such as glyoxal, benzaldehyde, citral and the like all share certain characteristics which indicate that volatiles from them should not be breathed, and contact or ingestion should be avoided.

While benzaldehyde and citral are considered edible aldehydes, that use is restrained to extremely small amounts as flavorings. Concentration above those found in flavoring levels should be avoided and persons should not be unnecessarily exposed to contact with or volatiles arising from these materials.

Glyoxal is not an aldehyde known in waste treatment, its use in the chemical composition of the present invention is disclosed herein. Glyoxal (ethanedial, biformyl, diformyl, oxaldehyde, $C_2H_2O_2$) demonstrates very low toxicity and low to no vapor at typical ambient conditions. Its boiling point being 51° F., glyoxal is an oxidation product of acetaldehyde. It demonstrates a very low toxicity even upon ingestion and demonstrates virtually no fumes or toxic vapors under normal ambient conditions of use such as within typical practical conditions encountered for treatment of body wastes. Glyoxal is considerably less corrosive with metals in which it comes in contact than either formaldehyde or glutaraldehyde. The $LD_{50}$ in rats, guinea pigs: 2020, 760 mg/kg, H. F. Smyth et al., J. Ind. Hyg. Toxicol. 23, 259 (1941). Its use in waste treatment as a primary ingredient to replace formaldehyde and glutaraldehyde is not known to or practiced by the art. Glyoxal does not form irritating or toxic volatiles in air under normal ambient conditions of use for treatment of body wastes. Upon ingestion by test animals, it is approximately 1,000 times less toxic than formaldehyde and on the order of 300 times less toxic upon ingestion or skin contact than glutaraldehyde.

When added to septic sewage wastes including manures, glyoxal is equally as effective in reduction of septicity and surpassingly superior to either formaldehyde or glutaraldehyde. It also has the important advantage that unlike either formaldehyde or glutaraldehyde body wastes cannot be over treated to a point where an excess will result in toxic vapors which would place workers and users at risk under work and use conditions for treating such wastes.

SUMMARY OF THE INVENTION

A composition and method for reducing stench and septicity from animal waste comprising a sulfur and oxygen-bearing component and one or more aldehydes and/or one or more ketones is disclosed. The sulfur and oxygen-bearing component is selected from the group consisting of sodium bisulfite, potassium bisulfite, lithium bisulfite, sodium metabisulfite, potassium metabisulfite, lithium metabisulfite, sodium hydrosulfite, potassium hydrosulfite, lithium hydrosulfite and hydrogen sulfite. The aldehyde is selected from the group consisting of formaldehyde, glyoxal, glutaraldehyde, benzaldehyde, acetaldehyde, butryaldehyde, cinnamaldehyde, salicylaldehyde, citral, glycolic aldehyde, paraldehyde, metaldehyde, heptylaldehyde, octylaldehyde, anisaldehyde, and decylaldehyde. The ketone is selected from the group consisting of diacetyl, ionone, pseudo-ionone, acetylacetone, 3-buten-2-one, mesityl oxide, acetone, methyl ethyl ketone, diethyl ketone and dipropyl ketone.

Most preferably, the aldehyde is formaldehyde and the sulfur and oxygen-bearing component is sodium bisulfite. The preferred amounts are between about 1 weight percent and about 35 weight percent formaldehyde and between about 2 weight percent and about 50 weight percent sodium bisulfite. The most preferred amounts are about 5 weight percent formaldehyde and about 16 weight percent sodium bisulfite.

A surfactant can be added to the composition. The surfactant is selected from the group consisting of cationic surfactants, non-ionic surfactants, amphoteric surfactants, anionic surfactants, and zwitterionic surfactants.

A metal can be added to the composition. The metal is selected from the group consisting of zinc, copper, aluminum, iron, salts thereof, zeolites thereof, oxides thereof, carbonates thereof, hydroxides thereof, hydrates thereof, and Bordeaux mixtures thereof.

DETAILED DESCRIPTION OF THE PREFERRED EMBODIMENTS

I. OVERVIEW

It has been discovered that highly safe products comprised of or including carbonyls selected from the group consisting of aldehydes and/or ketones and sulfur and oxygen-bearing components can be employed for reduction of stench and septicity of body wastes with equal or greater effectiveness than the aldehyde and/or ketones alone.

More importantly, such chemical compositions containing the aldehydes and/or ketones and sulfur and oxygen-bearing components, even when comprised of one or more aldehydes and/or ketones, and even when one or both are normally toxic, are under virtually all use conditions both effective to the purpose, and innocuous and safe to use. Moreover, such chemical compositions made therefrom are at least as, or more, effective than aldehydes and/or ketones when used alone to reduce stench and septicity of body wastes. Such chemical compositions exhibit no stench, no toxic volatiles and no contact toxicity.

It has been discovered that an alkali metal ketone or aldehyde bisulfite effectively reduces stench and septicity of body wastes and manure. The term "alkali metal ketone or aldehyde bisulfite" as used herein is intended to encompass any combination of the disclosed aldehydes, ketones, and sulfur and oxygen-bearing components. A pure alkali metal aldehyde bisulfite, a pure alkali metal ketone bisulfite, a mixture of one or more alkali metal aldehyde bisulfites, a mixture of one or more alkali metal ketone bisulfites, or a mixture of one or more alkali metal aldehyde bisulfites and alkali metal ketone bisulfites, with or without various diluents, carriers or other action-improving ingredients, can be safely utilized directly in body wastes or body waste receiving containers to safely neutralize stench and septicity.

Regarding the carbonyls selected from the group consisting of aldehydes and ketones, alkali metal ketone or aldehyde bisulfites may be produced from one or a plurality of sulfur or nitrogen active aldehydes and/or ketones. Except for acrolein, crotonaldehyde and propionaldehyde, which form only irreversible aldehyde bisulfite compositions, almost any aldehyde or combination thereof may be used. However, in general, those preferred may be selected from the group including, in order of preference, formaldehyde, glutaraldehyde, benzaldehyde, glyoxal, acetaldehyde, butryaldehyde, cinnamaldehyde, anisaldehyde, salicylaldehyde, citral, glycollic aldehyde, paraldehyde, metaldehyde, heptylic, octyl and decyl aldehydes. A very advantageous form of aldehyde is the dialdehyde formed in situ with the anhydroglucose molecule when it is converted by a strong oxidant such as periodic acid to dialdehyde starch. This may be accomplished by addition of alkaline earth metals sodium or potassium and sulphur radicals such as bisulfite ($NaHSO_3$), sodium dithionate ($NaS_2O_4$), alkaline metal and amine sulfur radical complexes. The result is a useful liquid or powdered form of alkali metal aldehyde bisulfite which may serve as an additive to animal wastes to reduce stench and septicity. Many ketones are effective aids for stench reduction and prevention and also provide generally superior penetrating qualities that may result in facilitating stench and septicity reduction. While almost any ketone can be used, those preferred may be selected from the group consisting of, in order of preference, diacetyl, ionone, pseudo-ionone, acetylacetone, 3-buten-2-one, mesityl oxide, acetone, methyl ethyl ketone, diethyl ketone and dipropyl ketone.

Those aldehydes and ketones, such as acrolein, crotonaldehyde and the like, which form irreversible compositions with alkali metals, are functionally useless in the present invention. With the exception of benzaldehyde, which demonstrates much greater stench reduction capacity than predictable, anisaldehyde and citral and the other highly aromatic aldehydes generally employed in perfumes and used as food flavorings are more useful as aldehyde or ketone co-additions with bisulfite, sulfide, and other sulfur and oxygen-bearing components. It is sometimes advantageous to include them even though alone they make only a moderate to weak contribution to overall stench and septicity reduction. When freed, they can contribute to penetration and dispersion of co-ingredients, to vapor-to-vapor reduction, and also provide a pleasant and non-noxious aroma which can provide a fresh background which is sometimes advantageous as a product accessory.

Regarding alkali metals, sodium, potassium and lithium are preferred, while others described herein can also be employed. The alkali metal ketone or aldehyde bisulfites most useful in this invention thus include sodium ketone or aldehyde bisulfite, lithium ketone or aldehyde bisulfites, and potassium ketone or aldehyde bisulfite. When formaldehyde is employed, the compound sodium formaldehyde bisulfite has the chemical formula $HOCH_2SO_3Na$, and is also known as formaldehyde sodium bisulfite and sodium hydroxymethane sulfonate. The compound potassium formaldehyde bisulfite has the chemical formula $HOCH_2SO_3K$, and is also known as formaldehyde potassium bisulfite and potassium hydroxymethane sulfonate. The compound lithium formaldehyde bisulfite has the chemical formula $HOCH_2SO_3Li$.

Regarding sulfur and oxygen-bearing components employed in the present invention, a bisulfite is preferred (e.g. sodium bisulfite); but metabisulfites (e.g., sodium metabisulfite), sulfites (sodium hydrosulfite), sulfides (e.g. hydrogen sulfide) and other sulfur and oxygen-bearing components may be employed. The term "sulfur and oxygen-bearing component" as used herein expressly includes all of the above chemical compositions.

The alkali metal ketone or aldehyde bisulfite may be utilized in dry form with a variety of active or inert materials, such as surfactants, metals, aromatics, diluents, carriers, excipients, lubricants, disintegrants, and/or colorants. A diluent (tricalcium phosphate) is an inert material which can be used to reduce the concentrations of active materials. Salt may be used as a carrier. Suitable diluents and carriers for use with alkali metal ketone or aldehyde bisulfites include salt and other similar, nonreactive, neutral electrolytes, such as sodium citrate and potassium chloride, and non-electrolytes and insoluble salts such as starch, sugars, clays, and calcium sulfate. An excipient, such as starch, and inert materials may be used as a binder for pellets or tablets. Starch converted to dialdehyde starch may actually be used as one of the aldehydes for forming compositions with alkali earth metal sulfites, sulfides or other sulfur and oxygen-bearing components.

Other excipients which may be used with alkali metal ketone or aldehyde bisulfites are hydrocolloids including the polymers and gums (e.g., cellulose gum and povidone), and starches. A lubricant or encapsulant such a monosodium or magnesium stearate may be used to segregate components which might otherwise prematurely react with aldehyde or ketone, and are useful to reduce friction during compression, extrusion or pelleting. Suitable lubricants for use with alkali metal ketone or aldehyde bisulfites include fatty acid salts such as calcium stearate or magnesium stearate, and paraffinic compounds, paraffin wax, and stearic acid. A disintegrant may be employed to cause pellets, tablets, and boluses to disintegrate under appropriate use conditions. Suitable disintegrants for use with alkali metal ketone or aldehyde bisulfites include polymers such as cross linked povidone, and effervescent mixtures such as sodium bicarbonate/citric acid. A colorant is an inert material which imparts color, or even murkiness, which is sometimes desirable in portable and other toilets pre-loaded with water. Suitable colorants for use with aldehydes and/or ketones include pigments such as rose madder, and non-oxidizing dyes such as acriflavine.

Both acids and alkalies hasten the decomposition of alkali metal ketone or aldehyde bisulfites. Consequently the different product forms, whether liquid or dry form, must either be buffered or otherwise protected from decomposition if moisture levels combine with ingredients to create an alkaline or acidic environment outside a range of about 6.0 to about 8.0.

When a non-water soluble aldehyde or ketone is desired for forming the composition, it is convenient to include a surfactant during the makeup phase to facilitate formation of the composition (for example, when benzaldehyde is combined with sodium metabisulfite). Added surfactants are usually associated in the composition, being readily carried in either a concentrated liquid or solid composition. "ARLASOLVE" (polyoxyethylene 20 isohexadecyl ether) and "BARLOX" (N-alkyl-N, N-dimethylamine oxide) are preferred surfactants, but others may also be used, provided either their pH is within the critical stable range of the composition formed, or that the pH is buffered to conform within that range. The associated surfactant also increases solubility and dispersion, which results in reduced septicity. Almost any surfactant which is effectively between the pH ranges of from about 6 to 6.5 up to about 8.0 to 8.5 can be used provided that it is either already within that range of pH or is buffered to within that range. The order of preference is from that which provides the most supporting functionalities, generally the cationics, followed by non ionics, amphoterics, anionics and so called zwitterionic surfactants.

A cationic surfactant is usually preferred due to its capacity to act as an emulsifier for forming the composition, its ready association with the composition in any form, its disposal of the composition upon application, and because cationics, as a rule, add significantly not only to stench reduction but also to septicity reduction. Cationics containing benzalkonium chloride and other equivalent disinfectants, such as iodophores or bromophores, are most preferred.

II. ALKALI METAL ALDEHYDE BISULFITE

One of the simplest forms of treating agent is comprised of a sulfur and oxygen-bearing component such as a bisulfite or a sulfite and preferred aldehydes such as formaldehyde, glutaraldehyde, glyoxal, acetaldehyde, benzaldehyde or one of the other aldehydes such as listed above. Each of the aldehydes mentioned has advantages and drawbacks. Of course, the chemical composition formed overcomes all of the immediate disadvantages of all aldehydes, including any inherent toxicity or noxiousness (such as irritating or poisonous volatiles).

EXAMPLE 1

To make a working solution of formaldehyde sodium bisulfite $CH_3NaO_4S$ (Mole weight 134.09) for prevention and/or reduction of stench and septicity of body waste:

|  | PREFERRED PARTS | ALLOWED RANGE (%) | PREFERRED PERCENTAGE |
| --- | --- | --- | --- |
| FORMALDEHYDE | 29 | 1–35 | 5% |
| SODIUM BISULFITE | 100 | 2–50 | 16% |
| WATER (50 to 55° C.) | 480 | 49–97 | 79% |

Ingredients are mixed in a water cooled jacket. The reaction is exothermic and should preferably be maintained between suggested operating temperatures. Temperatures employed are not critical, provided that adequate time is allowed if run at colder temperatures than suggested, or that appropriate enclosed vessels for condensing fugitive vapors and cooling to prevent boiling are available. Powder may be made by continued heating and removal of water vapors until a minimum of about 25 to 30 percent reduction of water. Product may be decanted, preferably cooled and filtered, evaporated or otherwise dried. A stable, odorless, readily water soluble, fine pure white crystalline powder is formed.

Depending on condition and type of body waste to be treated, as well as on application conditions, a typical treatment range for body wastes at 20–25% solids of finished undiluted wet product is 75 to 350 mls. For a 10% moisture powder of the product: 15 to 75 grams. For a 40 gallon holding tank, a precharge of 200 to 250 mls of liquid or about 40 to 60 gms of powder would be adequate.

A wide variety of aldehydes and ketones may be formulated in the same manner. Glutaraldehyde forms a less white end product which precipitates more readily. Benzaldehyde is very difficult to bring into reaction due to its oily nature and a small quantity of surfactant with a pH within stability ranges is preferred. Benzaldehyde precipitates during formation and may be removed either continuously or in the same manner as formaldehyde. The precipitate is coarser, tending toward agglomeration. It is water insoluble unless a solvent such as a ketone, or a surfactant or other emulsification aid has been added. "ARLASOLVE" is a preferred surfactant, ethyl or methyl alcohol, mesityl oxide, methyl ethyl ketone or other solvent may be used; preferably at between 3 to 12% by weight of the benzaldehyde. The addition of benzaldehyde to a more readily soluble aldehyde such as formaldehyde, acetyl aldehyde and the like may also serve to decrease the solubility of the soluble aldehyde and improve the solubility of benzaldehyde. Glyoxal also precipitates during formation. It is slowly soluble in aqueous solution and forms yellow complexes when reacted with animal body wastes.

III. ALKALI METAL KETONE OR ALDEHYDE BISULFITE

EXAMPLE 2

To make a working solution of any composition of aldehydes and/or ketones and sulfur and oxygen bearing components of the present invention for reduction of stench and septicity of body waste:

|  | PREFERRED PARTS | ALLOWED RANGE (%) |
| --- | --- | --- |
| R'1 ALDEHYDE or KETONE (X) | X | 0.10–99 |
| BISULFITE* (Y) | (X + Y)5.1 | 5.00 ±4 |
| WATER (50 to 55° C.) (W) | 4.0[(X + Y)5.1] | 5.00 ±4 |

*Sodium bisulfite, sodium metabisulfite, sodium hydrosulfite, hydrogen sulfide and alkali metal, potassium metabisulfite, potassium hydrosulfite, potassium bisulfite, lithium metabisulfite, lithium hydrosulfite, lithium sulfite and other sulfur and oxgen-bearing components.

The procedure described in detail in Example 1 is incorporated by reference into Example 2 herein in order to make the working solution of alkali metal ketone or aldehyde bisulfite.

IV. ADDITIONAL ALDEHYDE AND/OR KETONE

An improved product form over one containing a single ketone or aldehyde can be provided by inclusion of one or more additional aldehydes and/or ketones. After contact with body waste, formaldehyde, for example, once released from the chemical composition, will immediately react with the organic matter with which it is in contact. It is, however, a poor penetrant and the addition of aldehydes which have good solvent properties such as benzaldehyde or citral vastly improves formaldehyde's penetration capability, particularly where there are significant lipids involved. Of course, many of the ketones will also perform the same function. For some body wastes it may be necessary to select a plurality of additional aldehydes and/or ketones which may be brought together into an effective composite. In either event, any loss of stench or septicity reduction due to the displacement of some of a more powerful overall reactant is readily offset since not only do the additional aldehydes and/or ketones provide improved solvency, they also provide substantial stench and septicity reduction capacity. The net effect is improved stench and septicity reduction and the added benefit of improved cleaning of contact and containment surfaces as a result of the solventizing effects. Additionally, there is an overall improvement in stabilization and effectiveness since the additional aldehydes and/or ketones almost always add a significantly larger range of effect on body waste constituents responsible for generating stench and septicity.

EXAMPLE 3

To make a working solution of sodium ketone or aldehyde bisulfite with additional aldehyde and/or ketone(s) for reduction of stench and septicity of body waste:

|  | PREFERRED PARTS | ALLOWED RANGE (%) |
| --- | --- | --- |
| R'1 ALDEHYDE OR KETONE (X) | X | 0.1–99.0 |
| R'2 ALDEHYDE AND/OR KETONE ($X_1$) | $X_1$ | 99.0–0.1 |
| SODIUM BISULFITE (Y) | (X + Y)5.0769 | 5.0 ±3.0 |
| WATER (50 to 55° C.) (W) | 5[(X + Y)3.5] | 7.0 ±4.0 |

Selected surfactants may be added during the process to assist with composition formation, most particularly of non water soluble aldehydes and ketones. The range of addition for the above formulation is from about 5% to equal parts of R'1 aldehyde or ketone and R'2 aldehydes and/or ketones. It is preferred that the addition of other constituents occur in water prior to addition of the R'1 aldehyde or ketone and the R'2 aldehydes and/or ketones.

Ingredients may be mixed in the same manner and under the same conditions as provided in Example 1.

V. ADDITION OF SURFACTANT

Yet additional improvements are obtained when surfactants are included or at least added as a co-ingredient. Surfactants coupled to or associated with the other components not only can improve production but also enhance penetrating and dispersion abilities, yielding higher overall effectiveness of treatments. When surfactants are also selected from those possessing good microbicidal properties such as quaternary ammonium, benzalkonium chloride, bromophores and iodophores, overall reduction of septicity is also enhanced.

The product of any of the examples disclosed herein may be mixed with surfactants to provide convenient product blends. A typical example of a working formula for use in holding tanks is:

EXAMPLE 4

|  | PREFERRED PARTS | ALLOWED RANGE (%) | PREFERRED PERCENTAGE |
| --- | --- | --- | --- |
| LIQUID PRODUCT OF EXAMPLE #3 | 9 | 1–99 | 90% |
| SURFACTANT | 1 | 99–1 | 10% |
|  | 10 |  |  |

Ingredients may be mixed in the same manner and under the same conditions as provided in Example 1.

VI. ADDITION OF METAL, METAL SALT OR BORDEAUX SALT

As previously stated, alkali earth metal sulfites and bisulfites containing lithium, potassium and sodium are employed in the present invention. The addition of other stench and septicity reducing metals provides even greater overall effectiveness. Aldehyde and ketone bisulfites are unstable with many copper, zinc, iron and aluminum salts, except in extremely small concentrations. The addition of the selected metals can only be accomplished if both the selected alkali earth metal aldehyde or ketone and the selected metal or bisulfite metal salt are dry and/or the form of the metals used are or can be buffered, chelated, provided as a salt, ammoniated, coordinated with a ligand, or otherwise made available inside critical pH ranges within the particular pH stability range of the composition—usually from about 6.0 to 6.5 to 8.0 to 8.5 pH. Preferred metals are zinc, copper, aluminum, and iron or salts thereof. The preferred metals can be selected from those which are more stable with the chemical composition, such as copper, zinc, iron and aluminum silicates, zeolites, oxides, carbonates, hydroxides and hydrates. A preferred form of copper, zinc, iron and aluminum is as a Bordeaux salt. Bordeaux mixtures, for example, may be made over a wide range of lime to copper (usually as a sulfate) to which zinc, iron or aluminum salts can also be added. A preferred form is hydrated lime CaO, 8 to 10 lbs. (3.6–4.5 kg), copper sulfate, 4 to 6 lbs. (1.9–2.7 kg) in 100 gallons (378.5L) of cold water. Lime is defined by the ASTM definition C41–47 and includes any of the various chemical and physical forms of quicklime, hydrated lime and hydraulic lime. This is believed to produce a precipitate of tetracupric sulfate $4CuO.SO_3$ and pentacupric sulfate $5\ CuO.SO_3$. Combined with aldehyde(s) bisulfite and/or ketone(s) bisulfite as a treating agent the Bordeaux will, upon addition to body waste, begin to release soluble copper in response to septic microbes or to oxidation. Depending upon type and conditions of treatment available, metals may be added by separate treatment; partially or totally chelated with chelates including ethylenediaminetetraacetic acid (EDTA-$C_{10}H_6O_8N_2$), nitrilotriacetic acid (CHON); and ethyleneglycol-bis(β-aminoethyl ether)-N, N tetraacetic acid ($C_{14}H_{24}O_2N_2$), or sodium citrate. The metals may also be in the form of ammination or coordination compounds, or even coated or enrobed, for example, with stearate. When metals are added as buffered compounds, amphoteric metals such as zinc or zinc and aluminum are usually preferred. Where the application involves coating, copper and iron are usually preferred. In some locales the regional concentrations of metals may dictate a particular metal or group of metals regardless of that preferred normally. All of the foregoing metals are sufficiently effective that only minor adjustments in concentrations need be considered.

EXAMPLE 5

|  | PREFERRED PARTS | ALLOWED RANGE (%) | PREFERRED PERCENTAGE |
|---|---|---|---|
| LIQUID PRODUCT OF EXAMPLE 3 | 9 | 1–99 | 82% |
| SURFACTANT | 1 | 0–99 | 0% |
| BUFFERED METAL | 2 | 1–99 | 18% |
| SALT OR BORDEAUX TYPE METAL COMPOUND | 12 |  |  |

The protocol of Example 1 is followed.

Product of Example 5 may be made into a dry powder by any convection drying means. Tablets, pellets and boluses may be made from the powder for single use treating products.

Product of Example 5 may be manufactured into a dry form, i.e., powder, granule, flake, tablet, cake, pellet, bolus, capsule, liquid, gel, stick, film) with or without additives, or in a water solution with or without other compatible dissolved or suspended substances.

VII. ADDITION OF LIME

In an important variation, the alkaline ketone or aldehyde bisulfites may be added dry with any form of lime including portland cement, fly or other ash in a ratio of from about 1 to 200 to 1:1 aldehyde and/or ketone to lime to provide a powerful treatment product for reducing stench and septicity and for stabilizing sewage, sludge and manure body wastes. When mixed with body wastes at the rate of from about 1% to 40% of body waste by weight, the results are immediate reduction of stench and septicity and very high retention of nitrogens and sulfurs otherwise normally lost as pollution.

EXAMPLE 6

To 100 gallons of raw sewage centrifugate at 32% solids, one of the two following mixtures was added at the rate shown in a 200 gallon rotating drum mixer:

|  | PREFERRED PARTS | ALLOWED RANGE (%) |
|---|---|---|
| Dry powder mixture of product Example 5 | 4 lbs. | 0.1–100.0 |
| Portland cement fly ash | 56 lbs. | 99.9–0.0 |
|  | 60 lbs. |  |

RESULTS:

Control: The pH of the sewage before addition was about 8.7, the stench was of strong raw sewage type. Total ammonia measured inside the head space of the mixer was 16 to 18 ppm. Total nitrogen ~3.7#. A 24 hour sample of BOD was 161 ppm. Total plate, count too numerous to count (TNTC).

Sample #1: 60 pounds of portland cement fly ash was added and mixed into 100 gallons of control sewage in a rotating drum mixer. Within 2 minutes of the addition ammonia emissions measured in the head space of the rotating drum mixer was ~450 ppm. (Measurements were made with a Wilkes Miran II scanning infrared spectrometer.) The ammonia emission was above toxic limits. After 15 minutes the emission slightly abated, still showing ~400 ppm. All other stench characteristics of the sludge disappeared immediately after treatment, ammonia being the only detectable emission. The total 24 hour nitrogen was ~0.9#. The pH was 11.8. A 24 hour sample of BOD was 29 ppm. Total plate count 500.

Sample #2: 60 pounds of above dry mixture containing sodium formaldehyde/benzaldehyde bisulfite was added to 100 gallons of control sewage in a rotating drum mixer. Within 2 minutes the stench had almost completely disappeared and only 3 to 4 ppm ammonia was detected. Within 5 minutes the sample was stench free. No ammonia was detected. The pH was 7.4. Total nitrogen was 3.5#s. A 24 hour BOD sample was 1 ppm. Total plate count <50.

EXAMPLE 7

The same ratio of dry powder mix to portland cement fly ash as in Example 6 was used, but the composition of Example 1 containing formaldehyde was employed.

RESULTS:

Control: 100 gallons of concentrated poultry manure, solids 23%. The control sample exhibited an extremely powerful manure stench and yielded ammonia at the head space of ~130 ppm. After 24 hours the ammonia was the same. Beginning total nitrogen 6.3#s, after 24 hours it was 3.9. A 24 hour BOD of 185 ppm. Total plate count-TNTC.

Sample #1: A 100 gallon sample of concentrated poultry manure treated with 60 pounds of portland cement yielded a typical immediate reduction in poultry manure stench accompanied by a very high emission of ammonia at ~570 ppm at the immediate head space. After 24 hours total nitrogen was 1.6#s and the BOD 41 ppm. 24 hour head space ammonia was 65 ppm. Total plate count of product after treatment was 100.

Sample #2: 100 gallons of concentrated poultry manure treated with 56 pounds of dry portland cement and 4 pounds of dry product of Example 1 exhibited an immediate substantial reduction in stench. After 5 minutes head space ammonia was ~15 ppm and within 30 minutes was reduced further to ~3 ppm with no perceptible stench. After 24 hours the sample treated with the product of Example 1/ portland cement mix demonstrated no stench, an ammonia of 2 ppm, a BOD of 4 ppm and a total nitrogen of 5.8#s. Total plate count after treatment was <50.

STENCH: 1 to 10. Sensory panel 9 persons. Scale of malodor unpleasantness 0 to 10. Pain, painful to eyes, nostrils or lungs 0 to 10.
BOD: Biochemical oxygen demand, the quantity of dissolved oxygen in mg/L consumed by aerobic fermentation of sample over 5 days.

EXAMPLE 8

Summary: Samples of wastewater sludge were treated with formaldehyde and sodium metabisulfite and subjected to lime stabilization. Total nitrogen (TKN) and ammonia nitrogen levels were measured and compared to those of fresh sludge and lime-stabilized sludge (LSS), immediately after the lime addition step and after a 24-hour "airing out" period. On average, samples treated with the sodium formaldehyde metabisulfite demonstrated a 51.82% increase in TKN retention over untreated LSS. Sodium formaldehyde metabisulfite treated samples continued to hold a 39.10% edge over untreated LSS after 24 hours. Sodium formaldehyde metabisulfite treated samples also showed average increases in ammonia nitrogen retention over untreated LSS of 12.72% and 61.36% immediately after lime addition and after 24 hours, respectively.

Materials and Method: Wastewater sludge samples were obtained from the Maryville Waste Water Treatment Plant in Louisville, Tenn. The formaldehyde and sodium metabisulfite were supplied by Enviro-Chem Systems, Inc., a subsidiary of Monsanto Chemical Company, St. Louis, Mo. Lime used in the lime addition step is common "quick lime".

The LSS process utilizes a modified cement mixer with an 8-cubic yard rectangular hopper. Filtered wastewater sludge of various ratios between primary and secondary (mostly primary) is loaded in the hopper and processed in batch mode. After the hopper is filled, a screw-drive moves the sludge out through a cylindrical tunnel along the bottom of the hopper. Lime is added through a tee in the line and the screw-drive now doubles as a blender. Lime-added sludge (LSS) falls onto a 10-foot conveyor that dumps into a truck bed. Depending on the moisture level of the sludge, steam and ammonia release may start at the beginning of the conveyor or in the truck cab, and follows an exponential decline rate. Moisture acts as a heat sink that delays the steam generation and ammonia release. Other factors that affect the ammonia release include the quantity and quality of the lime used.

For runs 1 and 2, 0.5 gallon of sodium formaldehyde metabisulfite, diluted with 0.5 gallon of water, was added to the sludge in the hopper. A paddle mixer was started for ten minutes to blend the sodium formaldehyde metabisulfite into the sludge before the LSS process started.

For runs 3 and 4, 0.25 gallon of sodium formaldehyde metabisulfite diluted with 0.75 gallon of water was used.

For run 5, 1.5 gallons of sodium formaldehyde metabisulfite diluted with 1.5 gallons of water were used.

Fresh sludge samples were collected from inside the hoper each time it was filled. Lime added samples, both treated and untreated with sodium formaldehyde metabisulfite, were collected at the end of the conveyor. Piles of LSS, treated and untreated, were segregated at the dump site and samples collected from each pile after 24 hours.

Results: Samples were analyzed for TKN and ammonia nitrogen by Kenwill Laboratories in Alcoa, Tenn. The results are tabulated below.

TKN LEVELS IN LSS
Reported as ppm (ug/Kg) on a dry wt. basis

|  | Run 1 | Run 2 | Run 3 | Run 4 | Run 5 | Ave. | Inc. |
|---|---|---|---|---|---|---|---|
| Sludge | 93150 | 136000 | 150000 | 87000 | 203000 | 133830 | |
| LSS | 46200 | 43300 | ****** | 31500 | 82500 | 50875 | |
| LSS, 24 hr. | 52335 | 59500 | 62800 | 31900 | ****** | 51634 | |
| LSS and sodium formaldehyde metabisulfite | 118000 | 50800 | 81300 | 52900 | 83200 | 77240 | 51.82% |
| LSS and sodium formaldehyde metabisulfite, 24 hour | 67200 | 81200 | 60400 | 66500 | 83200 | 71820 | 39.10% |

AMMONIA NITROGEN LEVELS IN LSS
Reported as ppm (ug/Kg) on a dry wt. basis

|  | Run 1 | Run 2 | Run 3 | Run 4 | Run 5 | Ave. | Inc. |
|---|---|---|---|---|---|---|---|
| Sludge | 5754 | 2279 | 3377 | 2515 | 2209 | 3227 | |
| LSS | 658 | 679 | 717 | 755 | 651 | 692 | |
| LSS, 24 hr. | 456 | 462 | 445 | 401 | ****** | 441 | |
| LSS and sodium formaldehyde metabisulfite | 852 | 860 | 676 | 691 | 821 | 780 | 12.72% |
| LSS and sodium formaldehyde metabisulfite, 24 hour | 766 | 747 | 656 | 679 | 710 | 712 | 61.36% |

As can be seen above, TKN and ammonia nitrogen levels in fresh sludge vary greatly from batch to batch. It is highly probable that the sludge composition is non-homogeneous, rendering data from any random sampling event questionable. Averaging the results is a good solution for this type of data variability.

Average TKN level in untreated LSS appeared unchanged after 24 hours, indicating that the substantial total nitrogen loss (~60%) occurred immediately upon lime addition. This result correlated well with visual and olfactory observations, as well as "conventional wisdom". Treating the sludge with sodium formaldehyde metabisulfite before lime treatment reduced the TKN loss by 51.82%. Qualitatively, olfactory observation supports a reduction in ammonia odor. After a 24-hour "airing out" period, the amount of TKN retained in the treated samples is reduced by about 8%, but still showed a 39.10% improvement over untreated samples. It is not clear whether this "loss" is due to incomplete bonding between sodium formaldehyde metabisulfite and nitrogenous compounds, or due to data variability. It should also be noted that during the "airing out" period, the sludge piles were rained upon. Samples were collected from deep within the piles to minimize the effect of the added moisture.

Ammonia nitrogen levels in all samples are an order of magnitude below those of TKN. Average ammonia nitrogen level in untreated LSS declined 36% after 24 hours. Treated samples reduced this ammonia nitrogen loss by 12.72% at the end of the conveyor and 61.36% after 24 hours. Within the treated samples, an 8.7% decline in ammonia nitrogen retained is observed after 24 hours. This decline can be attributed to the same causes discussed above.

Conclusions: The data strongly suggest that sodium formaldehyde metabisulfite is effective in controlling nitrogenous odors and improving nitrogen retention in lime-stabilized sludge.

VIII. USE IN PORTABLE WASTE CONTAINMENT SYSTEMS

Portable waste containment systems or restrooms are widely utilized at remote work and other locations, such as construction sites, large temporary gatherings and high traffic areas which, for one reason or another, do not have available sewage services.

Portable restrooms may be constructed of a variety of materials, among which preformed fiberglass is typical. These units are designed to be readily portable and are moved onto a site for use for a specified period of time by an estimated number of persons. A typical unit is totally enclosed with adequate inner space to accommodate one person. The unit typically contains a holding reservoir which is pre-loaded with an amount of water deemed to give adequate liquid to dilute incoming waste sufficient to allow body wastes to be diluted for more compact storage and to permit some aqueous solvent for added treating agents. Formaldehyde is a typical treating agent. The water contained in the reservoir may range anywhere from several to as much as twenty gallons. A typical formaldehyde treatment may be from 2 to 16 or more ounces of 36% solution. Many proprietary products are available which also include dyes and other ingredients to aid in stench and septicity control.

EXAMPLE 9

The following example and test are illustrative of the comparison of a typical liquid formaldehyde and a typical glutaraldehyde formulation versus chemical compositions in accord with the present invention:

|  | PREFERRED PARTS | ALLOWED RANGE (%) |
|---|---|---|
| Sodium formaldehyde bisulfite/benzaldehyde dry, ratio of 4:1 (range 0:1 to 1:0) | 50 gms. | 0.10–99.90 |
| Copper/Bordeaux precipitate | 34 gms. | 0.10–99.90 |
| Magnesium stearate | 4 gms. | 0.00–80.00 |
| ARLASOLVE | 2 gms. | 0.00–99.75 |
|  | 90 gms. |  |

RESULTS:

Each of 6 30-gallon drums was pre-loaded with 2 gallons of tap water and raw sewage collected from the influent of a 1000 gallon septic tank serving 16 persons for a period of 5 days during work hours. The weight load per drum was a total of between 116 and 119 pounds.

Drum #1—control. No treatment was added to this drum.

Drum #2—Treated with 120 mls. of 20% formaldehyde solution to which was added 7 mls of "BARLOX 12" cationic surfactant.

Drum #3—treated with 120 mls of 20% solution of glutaraldehyde to which was added 7 mls of "BARLOX 12" cationic surfactant.

Drum #4—treated 120 mls of product of Example #4 to which was added 25 mls of "BARLOX 12" cationic surfactant.

Drum #5—treated with 120 mls of the product of Example #3—50% sodium formaldehyde/benzaldehyde solution (ratio of ~4:1 formaldehyde to benzaldehyde) to which was added 2 mls of "ARLASOLVE 12" cationic surfactant.

Drum #6—treated with 90 gram compressed tablet 2"×1.10" made of the product of Example 9.

| PRODUCT Drum #1 | MALODOR | PAIN | DRUM HEADSPACE | | DRAEGER SAMPLE | |
|---|---|---|---|---|---|---|
| DAY 1 | 4 | 2 | Ammonia | 0 | Formaldehyde | n/a |
| DAY 2 | 8 | 6 | Ammonia | 22 | Formaldehyde | n/a |
| DAY 3 | 10 | 6 | Ammonia | 32 | Formaldehyde | n/a |
| DAY 4 | 10 | 10 | Ammonia | 75 | Formaldehyde | n/a |

Day 1: Sewage stench moderate. Day 2: malodor much stronger, ammonia noticeable. Day 3: ammonia very strong unpleasant. Day 4: both malodor and ammonia overpowering. Initial BOD 90 ppm. Day 4 BOD 220 ppm.

| PRODUCT Drum #2 | MALODOR | PAIN | DRUM HEADSPACE | | DRAEGER SAMPLE | |
|---|---|---|---|---|---|---|
| DAY 1 | 1 | 9 | Ammonia | 0 | Formaldehyde | 65 |
| DAY 2 | 2 | 9 | Ammonia | 0 | Formaldehyde | 42 |
| DAY 3 | 4 | 6 | Ammonia | 15 | Formaldehyde | 15 |
| DAY 4 | 4 | 6 | Amnonia | 35 | Formaldehyde | 0 |

Day 1: almost no sewage malodor, strong formaldehyde vapors, unpleasant. Day 2: formaldehyde vapor still very unpleasant. Very slight sewage stench. Day 3: formaldehyde still present, sewage stench and some ammonia present. Day 4: Formaldehyde absent, sewage smell moderate, ammonia moderate. Day 4 BOD 55 ppm.

| PRODUCT | MALODOR | PAIN | DRUM HEADSPACE | | DRAEGER SAMPLE | |
|---|---|---|---|---|---|---|
| Drum #3 | | | | | | |
| DAY 1 | 1 | 6 | Ammonia | 0 | Formaldehyde | n/a |
| DAY 2 | 4 | 6 | Ammonia | 0 | Formaldehyde | n/a |
| DAY 3 | 6 | 4 | Ammonia | 5 | Formaldehyde | n/a |
| DAY 4 | 6 | 8 | Ammonia | 45 | Formaldehyde | n/a |

Day 1: almost no sewage malodor. Moderate glutaraldehyde malodor. Day 2: slight sewage malodor, moderate glutaraldehyde, no ammonia. Day 3: slight to moderate sewage malodor, slight ammonia, slight glutaraldehyde. Day 4: moderate sewage, moderate to strong ammonia. Day 4 BOD 67 ppm.

| PRODUCT | MALODOR | PAIN | DRUM HEADSPACE | | DRAEGER SAMPLE | |
|---|---|---|---|---|---|---|
| Drum #4 | | | | | | |
| DAY 1 | 2 | 6 | Ammonia | 0 | Formaldehyde | n/a |
| DAY 2 | 2 | 6 | Ammonia | 0 | Formaldehyde | n/a |
| DAY 3 | 4 | 4 | Ammonia | 5 | Formaldehyde | n/a |
| DAY 4 | 6 | 8 | Ammonia | 45 | Formaldehyde | n/a |

Day 1: very slight sewage malodor. Day 2: very slight sewage stench. Day 3: slight sewage stench and slight ammonia. Day 4: moderate sewage malodor, moderate to strong ammonia. Day 4 BOD 59 ppm.

| PRODUCT | MALODOR | PAIN | DRUM HEADSPACE | | DRAEGER SAMPLE | |
|---|---|---|---|---|---|---|
| Drum #5 | | | | | | |
| DAY 1 | 1 | 0 | Ammonia | 0 | Formaldehyde | 0 |
| DAY 2 | 2 | 0 | Ammonia | 0 | Formaldehyde | 0 |
| DAY 3 | 4 | 2 | Ammonia | 5 | Formaldehyde | 0 |
| DAY 4 | 6 | 6 | Ammonia | 35 | Formaldehyde | 0 |

Day 1: almost no sewage malodor. Day 2: very slight sewage malodor. Day 3: sewage and some ammonia present. Day 4: sewage smell moderate, ammonia moderate to strong. Day 4 BOD 53 ppm.

| PRODUCT | MALODOR | PAIN | DRUM HEADSPACE | | DRAEGER SAMPLE | |
|---|---|---|---|---|---|---|
| Drum #6 | | | | | | |
| DAY 1 | 1 | 0 | Ammonia | 0 | Formaldehyde | 0 |
| DAY 2 | 0 | 0 | Ammonia | 0 | Formaldehyde | 0 |
| DAY 3 | 2 | 1 | Ammonia | 2 | Formaldehyde | 0 |
| DAY 4 | 2 | 2 | Ammonia | 10 | Formaldehyde | 0 |

Day 1: almost no sewage malodor. Day 2: no sewage malodor. Day 3: very slight sewage and very slight ammonia present. Day 4: very slight sewage malodor, slight ammonia. Day 4 BOD 8 ppm.
STENCH: 1 to 10. Sensory panel 9 persons. Scale of malodor unpleasantness 0 to 10. Pain, painful to eyes, nostrils or lungs 0 to 10.
BOD: Biochemical oxygen demand, the quantity of dissolved oxygen in mg/L consumed by aerobic fermentation of sample over 5 days.

IX. USE IN AIRLINE, MARINE AND RECREATIONAL VEHICLE WASTE CONTAINMENT SYSTEMS

Airline, marine and recreational vehicle waste containment systems are generally comprised in part of aluminum alloys which are employed for their light weight and high strength-to-weight ratio. Aluminum alloys pose a unique problem in that many chemicals employed in waste containment corrode these alloys. The following examples provide two exemplary chemical compositions of the present invention which do not corrode aluminum alloys.

EXAMPLE 10:

| | PREFERRED AMOUNT | ALLOWED RANGE (%) |
|---|---|---|
| "ARLASOLVE" | 5.00 | 0.00–99.90 |
| Formaldehyde/benzaldehyde/ionone 20:4:1 | 60.00 | 0.10–99.90 |
| Copper/zinc/bordeaux | 20.00 | 0.10–99.90 |

-continued

|  | PREFERRED AMOUNT | ALLOWED RANGE (%) |
|---|---|---|
| Sodium citrate | 1.00 | 0.00–50.00 |
| Ethyl alcohol | 15.00 | 0.00–50.00 |
|  | 100.00 |  |

When the chemical composition of Example 10 was tested for corrosiveness against aluminum alloys, no significant pitting was present after 2 weeks. No vapors were detected.

Tested against aircraft/ship holding tank wastes. Example 10 resulted in 99% reduction in stench as measured by a stench panel consisting of 15 persons. The subjects were 8 females and 7 males. 50 mls. of Example 10 added to 4,000 mls. wet sample (30% solids) of holding tank waste reduced BOD in 4 separate samples from an average of 133 ppm to 21 ppm. Total average plate count all 4 samples was reduced from TNTC to 5,500.

EXAMPLE 11:

|  | PREFERRED AMOUNT | ALLOWED RANGE (%) |
|---|---|---|
| "BARDAC 2250" | 4.00 | 0.000–99.750 |
| Liquid sodium/formaldehyde/benzaldehyde/ionone 20:4:1 | 73.00 | 0.050–99.900 |
| Zinc chloroiodide | 8.00 | 0.025–99.900 |
| Copper gluconate | 8.00 | 0.025–99.900 |
| Sodium citrate | 2.00 | 0.000–50.000 |
| Ethyl alcohol | 5.00 | 0.000–50.000 |
|  | 100.00 |  |

Copper or zinc glycinate, as well as copper or zinc lactate may also be used. Zinc formaldehyde sulfoxylate may be used as a replacement for sodium formaldehyde/benzaldehyde/ionone at the same proportions. Zinc gluconate may also be used interchangeably with zinc chloroiodide in the same relative proportions.

When tested against Example 10 with 5–4,000 ml. samples of body wastes from aircraft holding tanks, Example 11 was equally as effective as Example 10 but resulted in 30% greater BOD reductions and substantially greater reductions in microbial plate counts.

In example 11, the 48-hour average total plate count of all 5 samples decreased from TNTC to 1,000.

EXAMPLE 12:

The following is an alternative to Example 10:

|  | PREFERRED AMOUNT | ALLOWED RANGE (%) |
|---|---|---|
| "VANWET 9N9" | 2 grams | 0.000–99.750 |
| Boric Acid | 10 grams | 0.025–99.900 |
| Formaldehyde/benzaldehyde/ionone 20:4:1 | 50 grams | 0.100–99.900 |
| Sodium citrate or zinc borate | 9 grams | 0.025–99.900 |
| EDTA | 2 grams | 0.000–30.000 |

While particular embodiments of the present invention have been described in some detail herein above, changes and modifications may be made in the illustrated embodiments without departing from the spirit of the invention.

I claim:

1. An antimicrobial composition for preventing stench from animal waste consisting of:

benzaldehyde;

formaldehyde metal bisulfite, said metal being selected from the group consisting of sodium, potassium and lithium; and a solvent.

2. An antimicrobial composition for preventing stench from animal waste consisting of:

benzaldehyde;

ionone;

aldehyde metal bisulfites, said metal being selected from the group consisting of sodium, potassium and lithium; and a solvent.

3. An antimicrobial composition for preventing stench from animal waste consisting of:

benzaldehyde;

aldehyde metal bisulfites, said metal being selected from the group consisting of sodium, potassium and lithium;

a second metal selected from the group consisting of copper and zinc; and a solvent.

4. An antimicrobial composition for preventing stench from animal waste consisting of:

benzaldehyde;

ionone;

formaldehyde metal bisulfite, said metal being selected from the group consisting of sodium, potassium and lithium;

a second metal selected from the group consisting of copper and zinc; and a solvent.

* * * * *